US010201306B2

(12) United States Patent
Ming (10) Patent No.: US 10,201,306 B2
(45) Date of Patent: Feb. 12, 2019

(54) METHOD AND SYSTEM FOR CAPTURING IMAGES FOR WOUND ASSESSMENT WITH SELF COLOR COMPENSATION

(71) Applicant: KONICA MINOLTA LABORATORY U.S.A., INC., San Mateo, CA (US)

(72) Inventor: Wei Ming, Cupertino, CA (US)

(73) Assignee: KONICA MINOLTA LABORATORY U.S.A., INC., San Mateo, CA (US)

( * ) Notice: Subject to any disclaimer, the term of this patent is extended or adjusted under 35 U.S.C. 154(b) by 213 days.

(21) Appl. No.: 15/251,968

(22) Filed: Aug. 30, 2016

(65) Prior Publication Data
US 2018/0055440 A1 Mar. 1, 2018

(51) Int. Cl.
H04N 13/257 (2018.01)
G06T 7/00 (2017.01)
A61B 5/00 (2006.01)
H04N 13/204 (2018.01)
(Continued)

(52) U.S. Cl.
CPC ............ *A61B 5/445* (2013.01); *A61B 5/0013* (2013.01); *A61B 5/0077* (2013.01); *A61B 5/1032* (2013.01); *A61B 5/7282* (2013.01); *G06F 17/3025* (2013.01); *G06F 17/30268* (2013.01); *G06K 9/6202* (2013.01);
(Continued)

(58) Field of Classification Search
CPC ............ H04N 13/0203; H04N 13/0257; A61B 5/445; A61B 5/0077; A61B 5/7282; G06K 9/6202; G06F 17/30268
See application file for complete search history.

(56) References Cited

U.S. PATENT DOCUMENTS 8,063,915 B2 * 11/2011 Champion ............. A61B 5/445
345/619
8,129,105 B2 * 3/2012 Zuckerman ........ A61B 5/14546
435/4
(Continued)

FOREIGN PATENT DOCUMENTS

JP 2010-22068 A 1/2010

OTHER PUBLICATIONS

International Search Report in related PCT application No. PCT/US2017/032173 dated Jul. 21, 2017.
(Continued)

*Primary Examiner* — Tsion B Owens
(74) *Attorney, Agent, or Firm* — Chen Yoshimura LLP (57) ABSTRACT

A wound image capture method that uses self color compensation to improve color consistency of the captured image and reliability of color-based wound detection. The method uses the skin tone of parts of the patient's own body for color calibration and compensation. In a data registration process, multiple parts of a new patient's body are imaged as baseline images and color data of the baseline images are registered in the system as reference color data. During subsequent wound image capture and wound assessment process, the same parts of the patient's body are imaged again as baseline images, and the wound and its surrounding areas are also imaged. Color data of the newly capture baseline images are compared to the registered reference color data and used to perform color compensation for the wound image.

18 Claims, 11 Drawing Sheets

(51) Int. Cl.
 A61B 5/103 (2006.01)
 G06F 17/30 (2006.01)
 G06K 9/62 (2006.01)
 G16H 50/00 (2018.01)
(52) U.S. Cl.
 CPC ........... *G06T 7/0024* (2013.01); *G16H 50/00* (2018.01); *H04N 13/204* (2018.05); *H04N 13/257* (2018.05); *A61B 2576/00* (2013.01); *G06T 2210/41* (2013.01)

(56) References Cited

U.S. PATENT DOCUMENTS

| | | | | |
|---|---|---|---|---|
| 9,042,967 B2 * | 5/2015 | Dacosta | ............... | A61B 5/0059 600/476 |
| 2010/0156921 A1 * | 6/2010 | McLennan | ........... | G06K 9/4652 345/589 |
| 2012/0059254 A1 * | 3/2012 | Lifan | ..................... | A61B 1/043 600/431 |
| 2012/0089031 A1 * | 4/2012 | Ince | ..................... | A61B 5/0261 600/476 |
| 2012/0259230 A1 * | 10/2012 | Riley | ................... | A61B 5/1072 600/477 |
| 2015/0150490 A1 * | 6/2015 | Xu | ....................... | A61B 5/6898 600/407 |
| 2018/0192029 A1 * | 7/2018 | Ming | .................... | G06T 7/0012 |

OTHER PUBLICATIONS

Written Opinion in related PCT application No. PCT/US2017/032173 dated Jul. 21, 2017.

* cited by examiner

METHOD AND SYSTEM FOR CAPTURING IMAGES FOR WOUND ASSESSMENT WITH SELF COLOR COMPENSATION

BACKGROUND OF THE INVENTION

Field of the Invention

The present invention relates to a device and method for wound assessment, and more particularly, it relates to a method and system for capturing visible injuries or wounds.

Description of Related Art

For many wound types, such as pressure ulcers, recovery times can be very long. To track wound progress and perform proper treatment, the first step is to capture images of the wound properly. The color of the wound can provide useful information for wound assessment. However, a challenge is that the color of an object can be perceived and captured differently due to different ambient light, different capture devices and different capture conditions including shutter speed, aperture diameter, etc. To compensate for color variations caused by the above factors, one way is to use a spectral irradiance meter or spectrometer, which gives high accuracy results but is expensive. Another way is to use standard color checkers (a board having patches of known colors) or customized color patches for color calibration, i.e., by capturing the wound images with the color checker alongside the wound. This method is less expensive; however, using additional device or color checker is very inconvenient in many clinic settings, especially for routine or daily procedures.

SUMMARY

Accordingly, the present invention is directed to a method for capturing images of a wound that substantially obviates one or more of the problems due to limitations and disadvantages of the related art.

An object of the present invention is to provide color compensation for wound images taken in routine or daily procedures without using any additional spectral measurement devices or color checkers.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve these and/or other objects, as embodied and broadly described, the present invention provides a method implemented in a system including an image capture device for using color images to assess a wound of a patient, which includes: during an initial registration stage: (a) capturing one or more first images of one or more baseline regions which are parts of the patient's body; (b) storing, in a database, the one or more first images and/or color data of the one or more first images; during a wound assessment stage: (c) retrieving, from the database, the one or more first images and/or color data of the one or more first images; (d) capturing one or more second images of the one or more baseline regions; (e) capturing a third image containing the wound and its surrounding area; (f) calculate color compensation data by comparing color data of the second images and corresponding color data of the first images, and compensating color values of the third image based on the calculated color compensation data; and (g) assessing the wound using the compensated third image containing the wound and its surrounding area.

Preferably, in step (a), each of the captured one or more first images include a color checker imaged together with the baseline region, the color checker being a physical object having a plurality of color patches with known color values. The color checker can be used to perform preliminary color compensation for the captured images.

Preferably, the method further includes: during the initial registration stage: capturing a fourth image containing the wound and its surrounding area; designating one or more regions of the surrounding area of the fourth image as secondary reference regions; and storing, in the database, the fourth image and locations of the designated secondary reference regions of the fourth image.

In another aspect, the present invention provides a computer program product comprising a computer usable non-transitory medium (e.g. memory or storage device) having a computer readable program code embedded therein for controlling an image capture device, the computer readable program code configured to cause the data processing apparatus to execute the above methods.

It is to be understood that both the foregoing general description and the following detailed description are exemplary and explanatory and are intended to provide further explanation of the invention as claimed.

DETAILED DESCRIPTION OF PREFERRED EMBODIMENTS

Figure 1:
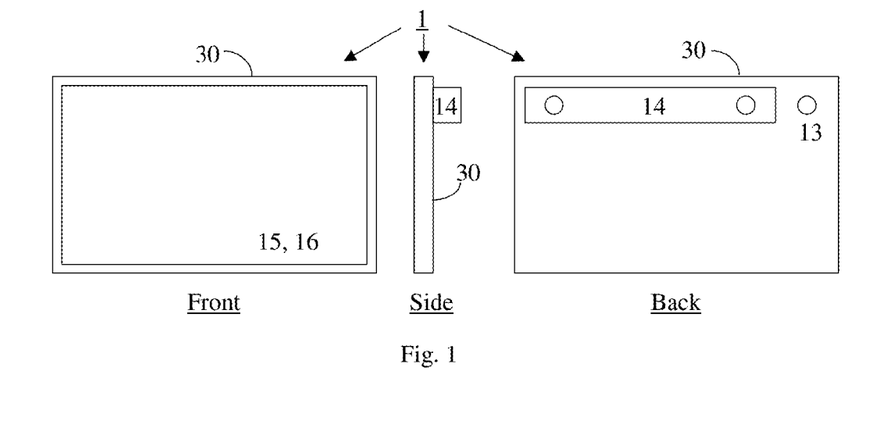
FIG. 1 is an illustration of an imaging device for wound assessment with a graphical user interface in accordance with an exemplary embodiment.
Figure 2:
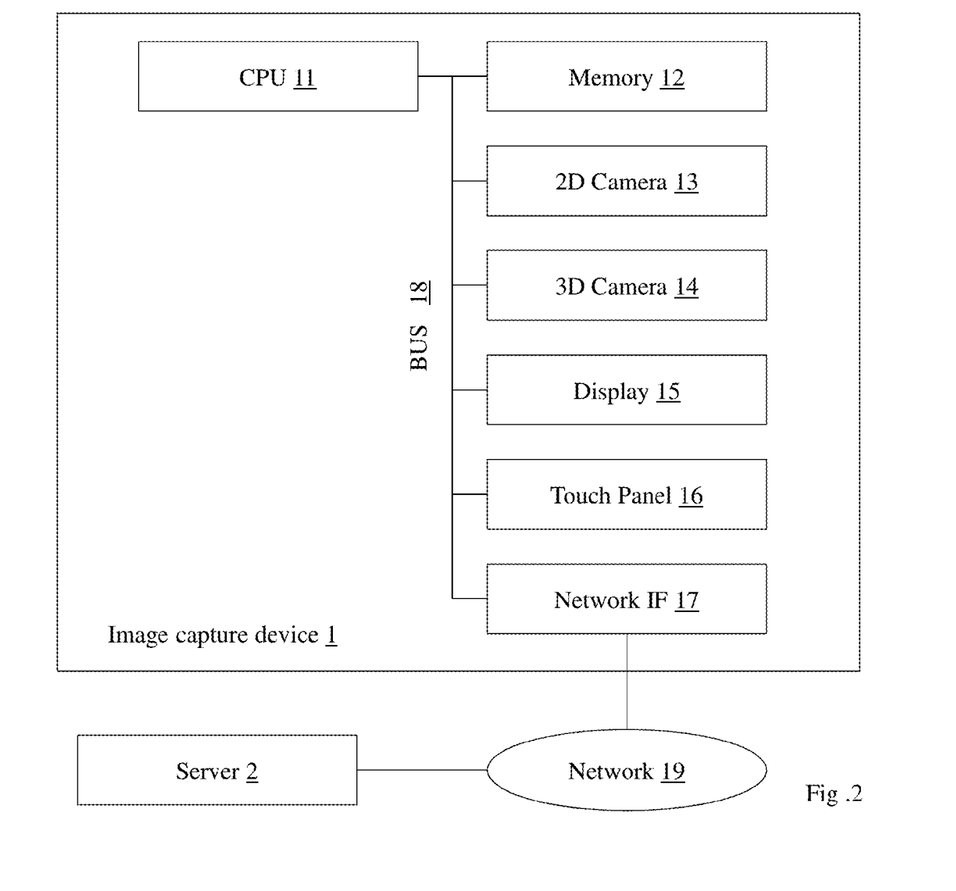
FIG. 2 is a schematic hardware block diagram showing the structure of the imaging device of FIG. 1.

FIG. 1 is an illustration of an imaging device 1 for wound assessment with a graphical user interface according to an embodiment of the present invention. FIG. 2 is a hardware block diagram showing the structure of the imaging device 1. As shown in FIG. 1, the device 1 includes a graphical user interface or screen 15, which preferably includes a touch screen or panel 16 on a front side. The device 1 also includes one or more cameras 13, 14, preferably in the form of a two-dimensional (2D camera) 13 and a three-dimensional (3D) camera 14 on a back side. For example, the imaging device 1 may be a tablet computer, for example, an iPhone®, an iPad®, Android enabled devices and/or other various handheld mobile devise, which includes one or more cameras having the ability to capture and generate 3D images. As shown in FIG. 1, the device 1 may be a tablet or tablet-like device having the user interface or display 15 and an outer housing 30.

Electrical components are positioned within the housing. The electronic components may vary depending on the particular functionality of the device 1. However, by way of example, the electronic components may include, for example, a communication interface 17, a processor 11, and a memory 12 storing computer executable programs. The imaging device 1 may communicate with a data processing and storage server 2 via a network 19. The method described below may be implemented by computer executable programs stored on the imaging device 1 and/or or the server 2 executed by the processor of the imaging device and/or the server.

Embodiments of the present invention provide a wound image capture method that uses self color compensation to improve color consistency of the captured image and reliability of color-based wound detection. The method uses the skin tone of parts of the patient's own body for color calibration and compensation. The skin tone of a new patient is registered in the system in a data registration process, and then used as a reference for color compensation later on during subsequent wound image capture and wound assessment. More specifically, in the data registration process, multiple parts of a new patient's body are imaged as baseline images and color data of the baseline images are registered in the system as reference color data. During a subsequent wound image capture and wound assessment process, the same parts of the patient's body are imaged again as baseline images, and the wound and its surrounding areas are also imaged. Color data of the newly capture baseline images are compared to the registered reference color data and used to perform color compensation for the wound image.

Figure 3:
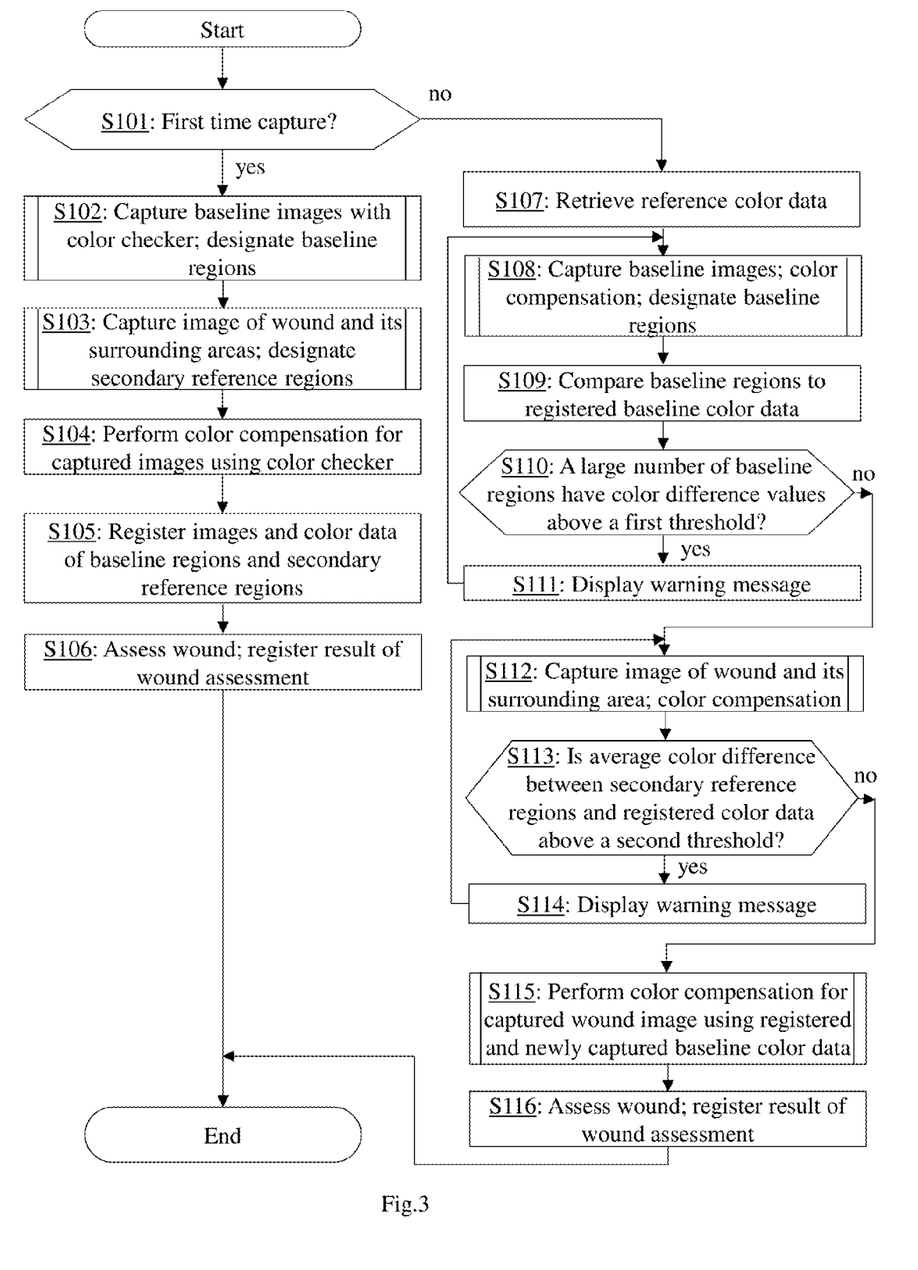
FIG. 3 schematically illustrates a wound image capture and color compensation process according to embodiments of the present invention.

FIG. 3 schematically illustrates a wound image capture and color compensation process according to embodiments of the present invention. FIGS. 4-9 schematically illustrate the details of various steps in the process of FIG. 3.

Referring to FIG. 3, the overall method includes two stages: In the first stage (registration stage, steps S102 to S106), performed the first time a wound is imaged for assessment ("yes" in step S101), reference colors are obtained from the patient's own body and registered in the system. The registration stage is performed only once. The second stage (wound assessment stage, steps S107 to S116) is performed the second and subsequent times when the wound image is captured in daily or routine procedure ("no" in step S101), where the registered reference colors are used to perform color compensation.

Referring to FIG. 3, the first stage (reference color registration) includes the following steps. First, multiple baseline images are captured on various parts of the patient's body together with a standard color checker, and appropriate areas in the images are designated as the baseline regions (step S102).

Preferably, the baseline regions are on parts of the body that (1) are not directly or frequently expose to sun light, (2) have skin tones that do not vary with health conditions, mood, or physical activity, and (3) are relatively flat. In some examples, the baseline regions may be on the stomach, back, inside of forearm or upper arm, etc. A color checker is a plate that has an arrangement of patches of printed colors having known color values; it is placed over or adjacent to the body when capturing the baseline images. Preferably, a light on the imaging device (e.g. a torch or flash) is turn on when capturing the images.

Figure 4:
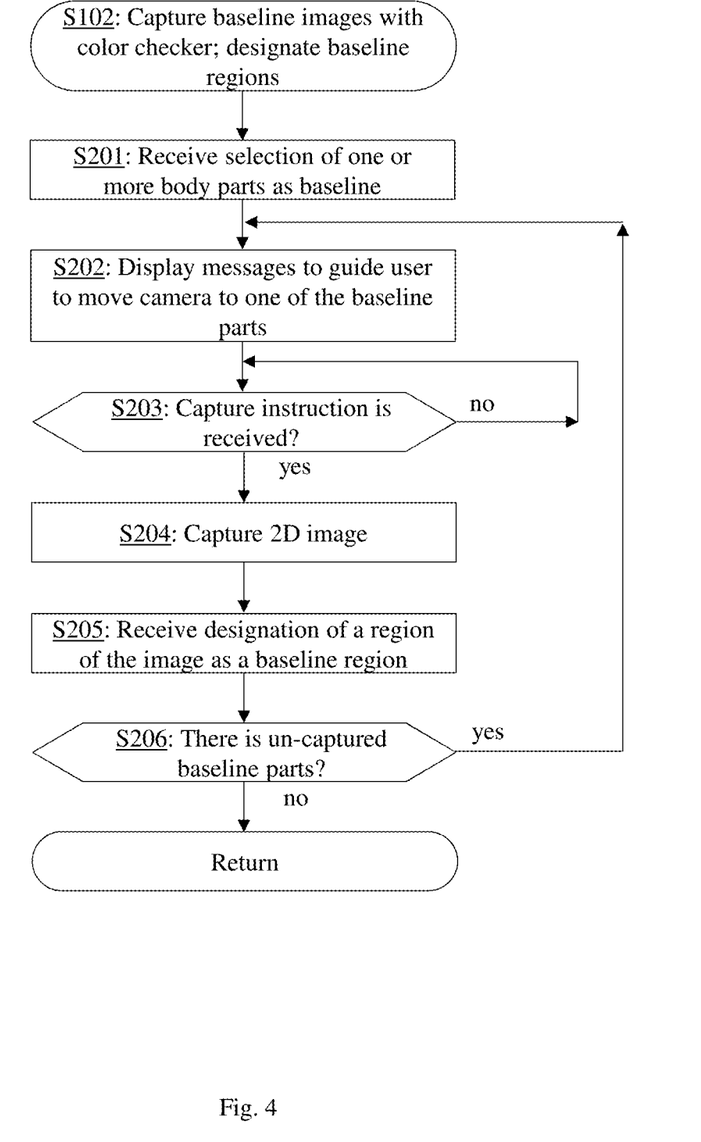
FIGS. 4-9 schematically illustrate the details of various steps in the process of FIG. 3.
Figure 10:
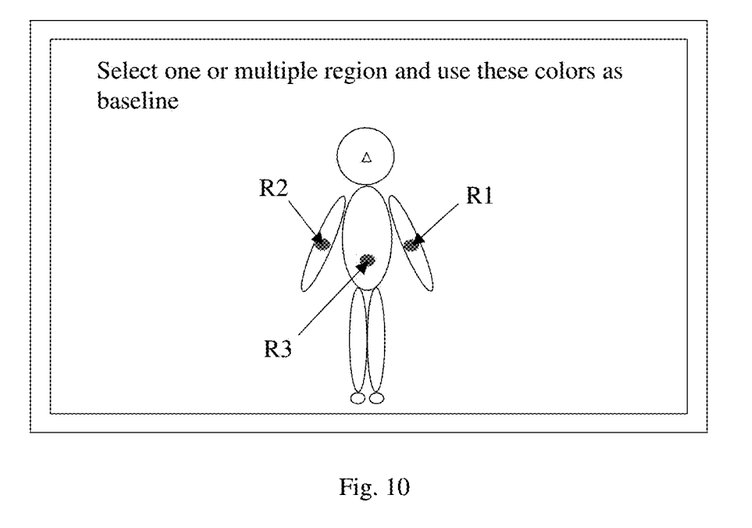
FIGS. 10-15 schematically illustrate exemplary displays on the imaging device in various steps of the process of FIG. 3.

FIG. 4 illustrates the details of step S102 according to one embodiment. First, the imaging device receives user selection of one or more parts of the patient's body to be used as baseline regions (step S201). This may be done, for example, by displaying on the imaging device a schematic representation of a body with indications that indicate body parts that are typically suitable for use as baseline regions, such as that shown in FIG. 10. The user can use the touch screen to select one or more of these parts for image capture.

Figure 11:
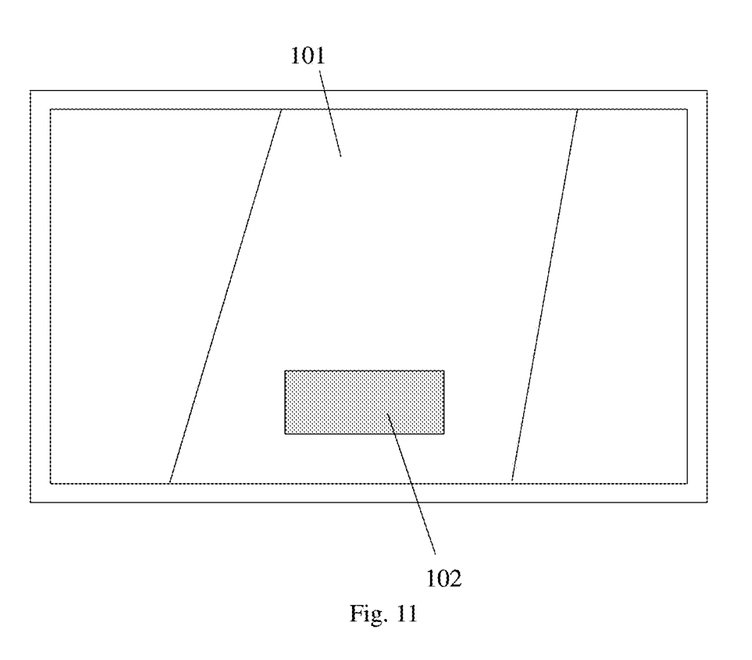

Then, the imaging device displays messages to guide the user to move the camera to one of the selected baseline regions and place the color checker adjacent to the region (step S202). The user gives a capture instruction (step S203) and the imaging device captures an image (a 2D image) (step S204). FIG. 11 schematically illustrates an exemplary display of a captured image of a baseline region, here, a part of the patient's arm 101, with a color checker board 102 placed over it. The imaging device then receives a user input to designate a specific region of the image as a baseline region to be used for color reference (step S205). The designation may be done by the user using the touch screen. For example, the imaging device may display a box, and the user is allowed to drag the box to a desired location. Steps S202-S205 are repeated until images of all selected baseline regions are captured ("no" in step S206).

Figure 8:
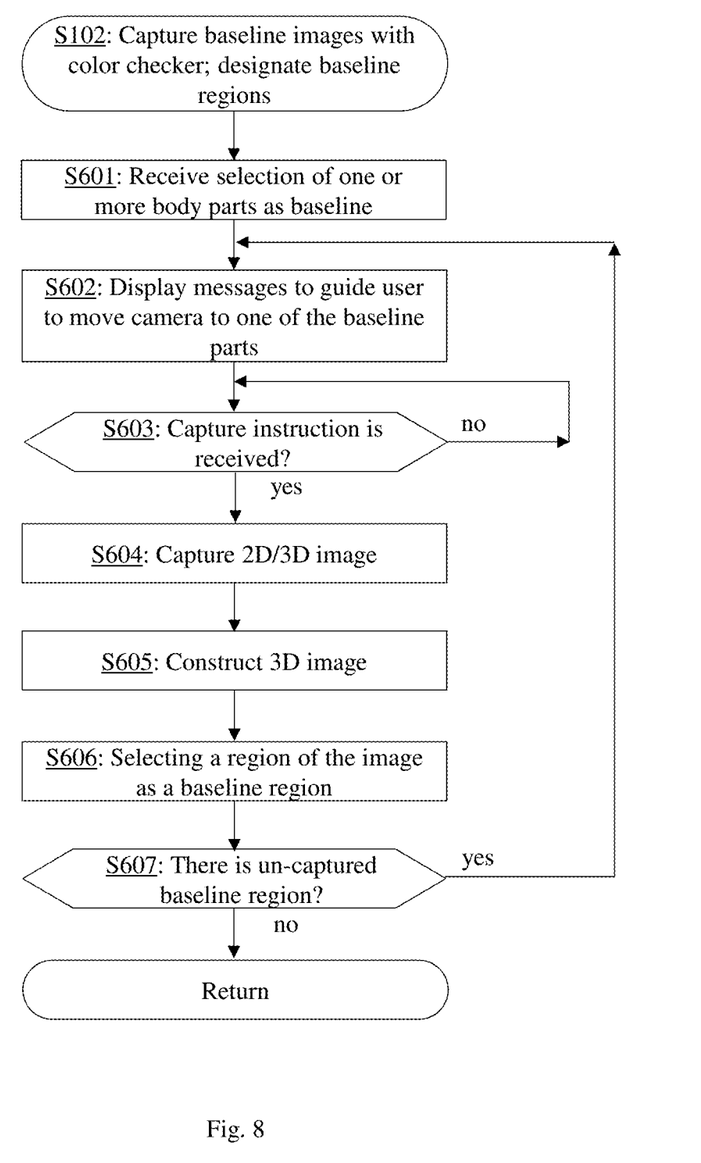

FIG. 8 illustrates the details of step S102 according to an alternative embodiment. Steps S601, S602, S603 and S607 are the same as steps S201, S202, S203 and S206. In response to a capture instruction, the imaging device captures stereo images (step S604) and constructs a 3D image from the stereo images (step S605). Then, the imaging device selects an area in the captured image to be used as the baseline region (step S606). For example, in this step, the imaging device may use the 3D image to detect flat areas suitable as the baseline region. The imaging device may also measure the color uniformity throughout the image and makes sure that the selected baseline region has a uniform color.

Referring back to FIG. 3, after step S102, one or more images of the wound to be assessed and its surrounding areas are captured, and one or more small regions in the surrounding areas are designated as secondary color reference regions (step S103).

Figure 5:
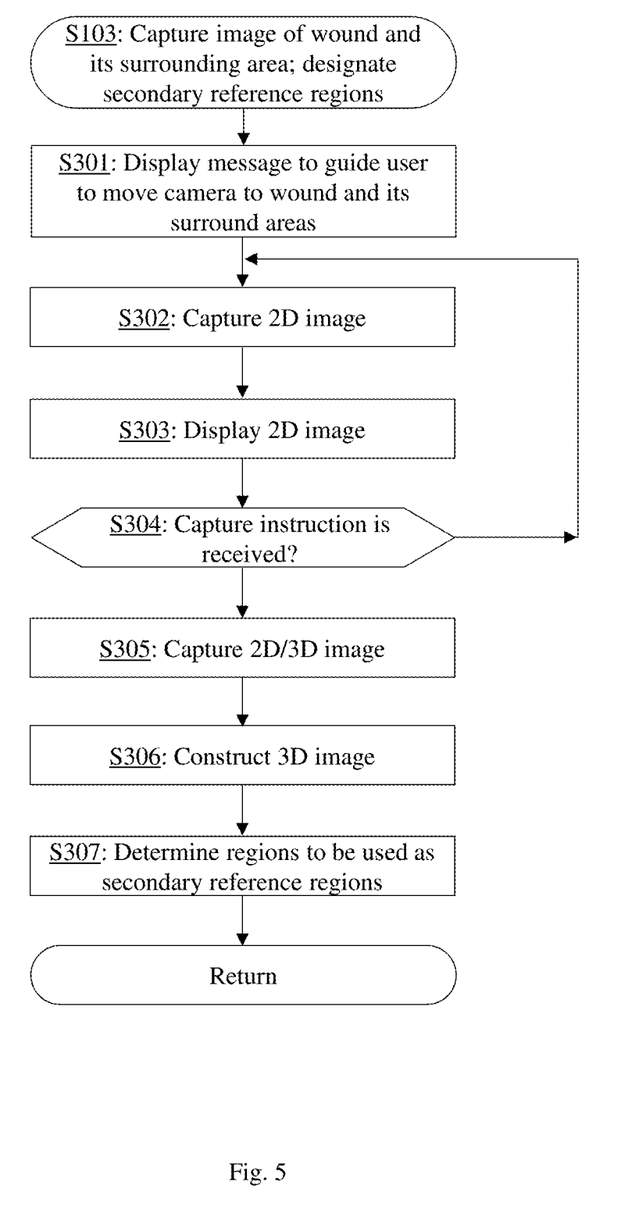

FIG. 5 illustrates the details of step S103 according to one embodiment. First, the imaging device displays messages to guide the user to move the camera to the wound and its surrounding areas (step S301). The imaging device captures (step S302) and displays (step S303) 2D images of the objects on the viewfinder and waits for the user to give a capture instruction (step S304). In response to the capture instruction, the imaging device captures stereo images of the wound and the surrounding areas (step S305) and constructs a 3D image (step S306). Preferably, a light on the imaging device (e.g. a torch or flash) is turn on when capturing the images.

Then, the imaging device determines one or more small regions of the surrounding areas in the captured image to be used as secondary color reference regions (step S307). Preferably, the secondary reference regions should be flat and on the same plane as the wound center or close to that plane. The imaging device uses the 3D image to determine whether a surrounding region is on or close to the same plane as the wound. The imaging device may also measure the color uniformity of the surrounding areas to ensure that each selected secondary reference regions has a uniform color. Alternatively (not shown), the selection of the secondary reference regions may be done manually by the user, e.g., using the touch screen (i.e. by dragging a displayed box). Typically, the image is captured so that the head-to-toe direction of the body is the up-down direction of the image; in such an image orientation, the secondary reference regions may be either above or below the wound, or to the left or right of the wound, or in any other direction.

Figure 12:
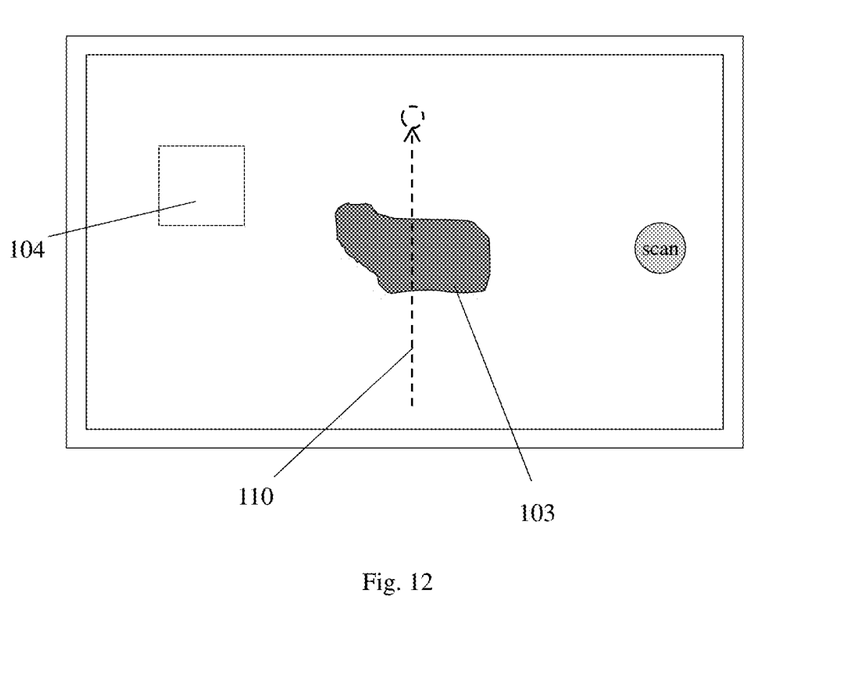

FIG. 12 schematically illustrates an exemplary display on the imaging device after step S307, showing the wound 103 and the designated secondary reference region 104. Optionally, a schematic indication 110 that indicates the head-toe direction of the body is overlaid on the image.

In step S103, the wound and its surrounding areas may be captured on the same image or in separate images. Capturing the wound and the surrounding areas on the same image is preferred if one captured image can cover the wound and its surrounding areas with enough details and contrast. In addition, if possible, it is even more preferable to capture the three regions, namely one of the baseline regions, the wound, and its surrounding areas, all in one image. For example, the patient may move his arm next to the wound, so that the inside of the arm can be captured in the same image with the wound and its surrounding areas.

Referring back to FIG. 3, after step S103, the imaging devices performs a preliminary color compensation for all the captured images (baseline and wound) based on the image of the color checker (stet S104). More specifically, a color balance (also referred to as chromatic adaptation) operation is applied to each baseline image that contains the color checker, to adjust the colors of the image until the color values of the color patches of the color checker in the image are approximately equal to the known color values of the corresponding patches of the color checker. Then, the same color balance (or an average from multiple baseline images) is applied to the other captured images to adjust their color. Any suitable color balance algorithm may be used, including but not limited to Von Kries's method, Bradford XYZ scaling, RGB scaling, etc.

The imaging device registers the preliminarily color-compensated images of the baseline regions and of the wound and its surrounding area, along with their color data, in the system (server and/or imaging device) (step S105). This includes storing, in a database (either locally on the image capture device or on the server), the above preliminarily color-compensated images, the locations of the baseline regions on the patient's body, the locations of the secondary reference regions, the average color values (e.g. RGB) of each baseline region and each secondary reference region (optional), and the color balance calculated based on the color checkers in step S104. The locations of the secondary reference regions can be identified as locations relative to the wound center and relative to a pre-defined direction of the body (e.g. head-to-toe), and the location of the baseline regions may be identified using predefined zone number on each limb, etc. Optionally, the original captured (un-compensated) images can also be stored. Alternatively, instead of whole baseline images, partial images of only the baseline regions in these images are stored.

Wound assessment may be performed using the wound captured image, and the result may be stored on the server and/or the imaging device (step S106, optional for the registration stage). The wound assessment procedure may include, for example, detecting the wound based on color and/or texture, measuring the width, height, and depth of the wound and the color of the wound, etc.

In the second stage (wound assessment), performed as a daily or routine procedure, the imaging device retrieves the registered reference color data for the baseline regions and secondary reference regions from the system (server and/or the imaging device) (step S107). The imaging device then displays messages to guide the user to move the camera to aim at the baseline regions one by one, and to capture images of the baseline regions (step S108). No color check is required in these baseline images.

Figure 6:
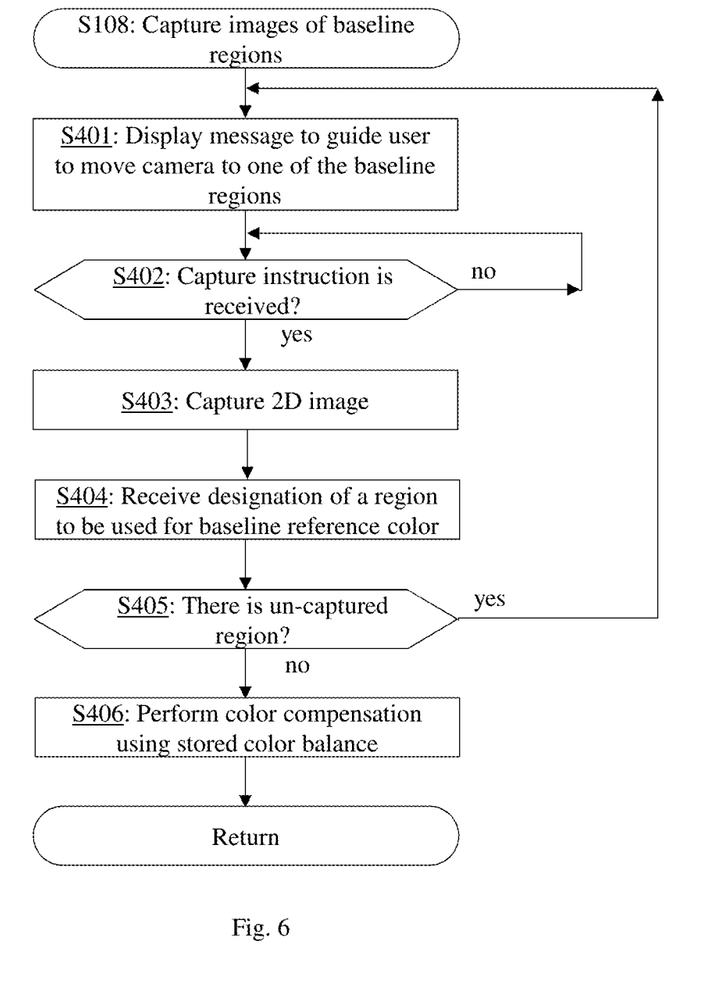
Figure 13:
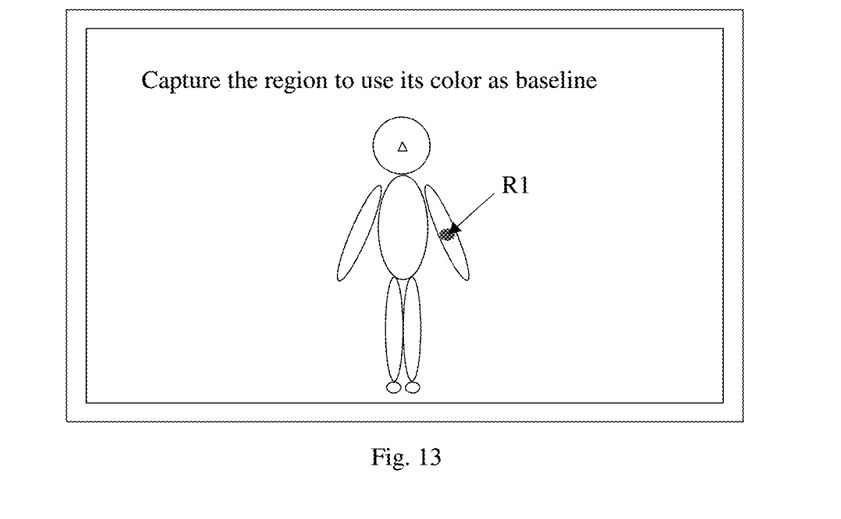

FIG. 6 illustrates the details of step S108 according to one embodiment. First, the imaging device displays messages to guide the user to move the camera to one of the baseline regions (step S401). FIG. 13 schematically illustrates an exemplary display in this step. As seen in this example, the display may include a schematic representation of a body (similar to that in FIG. 10) with indications that indicate body parts that were previously captured as baseline regions. Then, in response to a capture instruction (step S402), the imaging device captures a 2D image of the baseline region (step S403). The imaging device then receives a user input to designate a specific region of the image as a baseline region to be used for color reference (step S404), similar to step S205 during the registration stage. Steps S401-S404 are repeated until images of all baseline regions are captured ("no" in step S405). The imaging device then performs preliminary color compensation for the newly captured baseline images using the stored color balance, i.e. the color balance calculated based on the color checker in step S104 (step S406).

Figure 9:
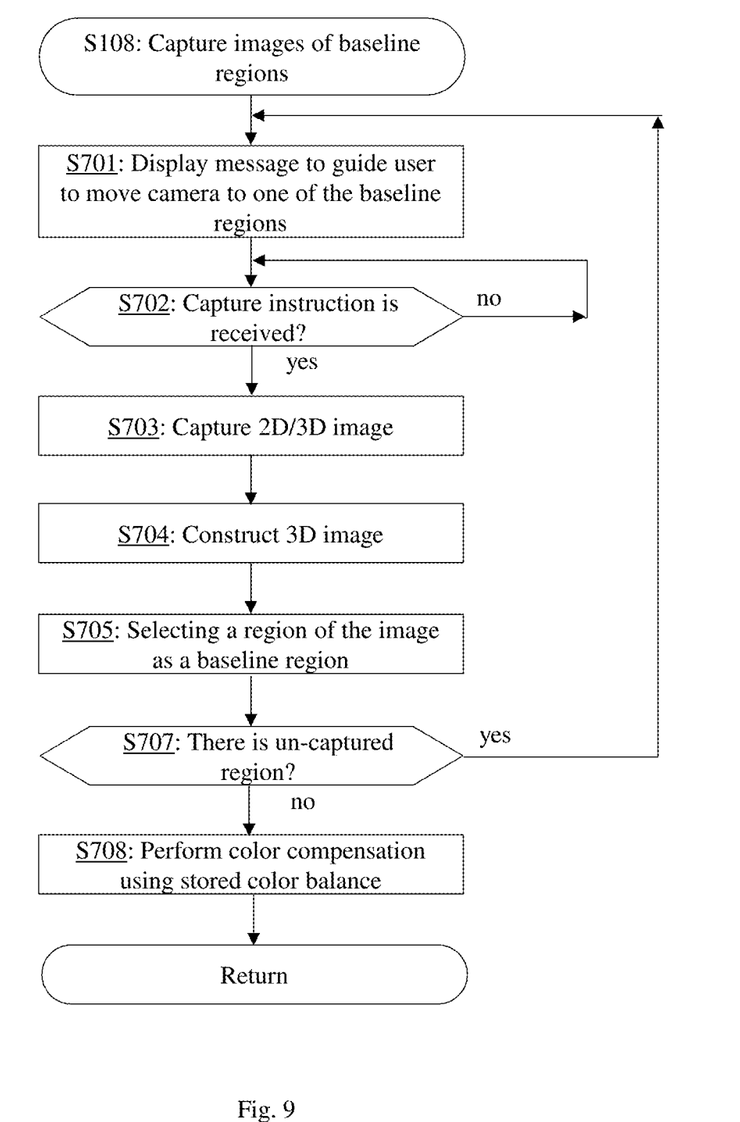

FIG. 9 illustrates the details of step S108 according to an alternative embodiment. Steps S701 and S702 are the same as steps S401 and S402. The imaging device captures stereo images (step S703) and constructs a 3D image (step S704). Then, the imaging device selects a region in the captured image to be used as the baseline region (step S705). This step is similar to step S606 in FIG. 8 during the registration stage. The imaging device then performs preliminary color compensation for the newly captured baseline images using the stored color balance, i.e. the color balance calculated based on the color checker in step S104 (step S708).

Referring back to FIG. 3, after capturing the baseline regions (including preliminary color compensation), the imaging device calculates the average color of each baseline region and compares them to the registered preliminarily color-compensated baseline color data (step S109). This step includes, for each newly captured baseline region, calculating a color difference value between the newly captured baseline region and the corresponding registered baseline region and comparing it to a first predetermined threshold value.

In one implementation, the color different value is calculated using $$dE=\sqrt{(R-R0)^2+(G-G0)^2+(B-B0)^2} \quad \text{(Eq. 1)}$$

where R, G, B are the average red, green and blue values of the newly captured baseline region and R0, G0, B0 are the average red, green and blue values of the corresponding registered baseline region. A suitable filtering technique may be applied to filter out those colors that are far away from the average values in the above calculation. The predetermined threshold value maybe, for example, dE=10 (when the RGB values range from 0 to 255). Other color spaces, such as XYZ, may also be used to calculate color difference.

If multiple baseline regions are processed and all or a large number of them (more than a threshold number) have color difference values above the first threshold, or if there is only one baseline region and its color difference value is above the first threshold ("yes" in step S110), the imaging device displays a warning message to guide the user to check imaging conditions e.g. ambient lighting, position of body parts, capture device settings, etc. (step S111) and the process goes back to step S108 to re-capture the baseline images. For example, the message displayed in this step may state: "A large number of baseline regions have color differences between the registered baseline and captured baseline that are too high. Please checking ambient lighting, device settings and captured location, and re-capture the baseline images." This process may be repeated until a sufficient number of baseline regions have color difference values at or below the first threshold.

If a sufficient number of newly captured baseline regions have color difference values at or below the first threshold ("no" in step S110), the newly captured baseline images are accepted, and one or more images of the wound and its surrounding areas are captured (step S112).

Figure 7:
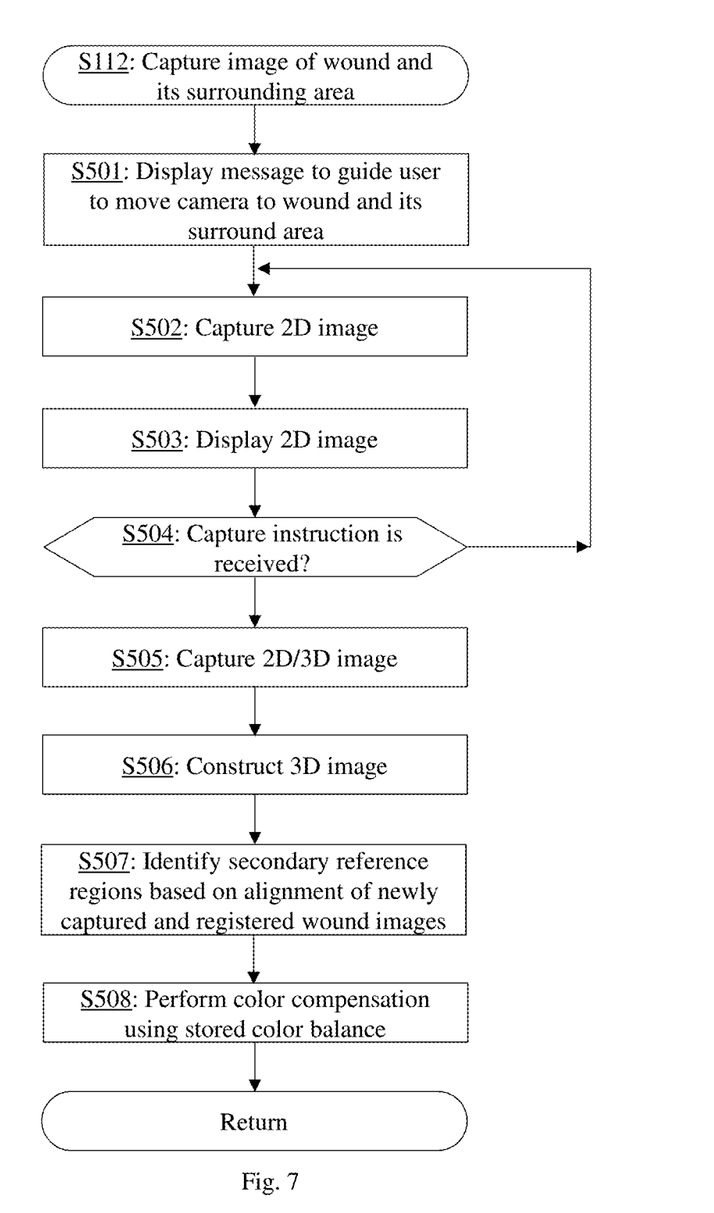

FIG. 7 illustrates the details of step S112 according to one embodiment. First, the imaging device displays messages to guide the user to move the camera to the wound and its surrounding areas (step S501). For example, the message displayed in this step may state: "Baseline check is successful. Move to wound area and capture image." In steps S502 to S506 (which are similar to steps S302 to S306 in FIG. 5 during the registration stage), stereo images are captured and a 3D image is constructed of the wound and the surrounding areas.

Figure 14:
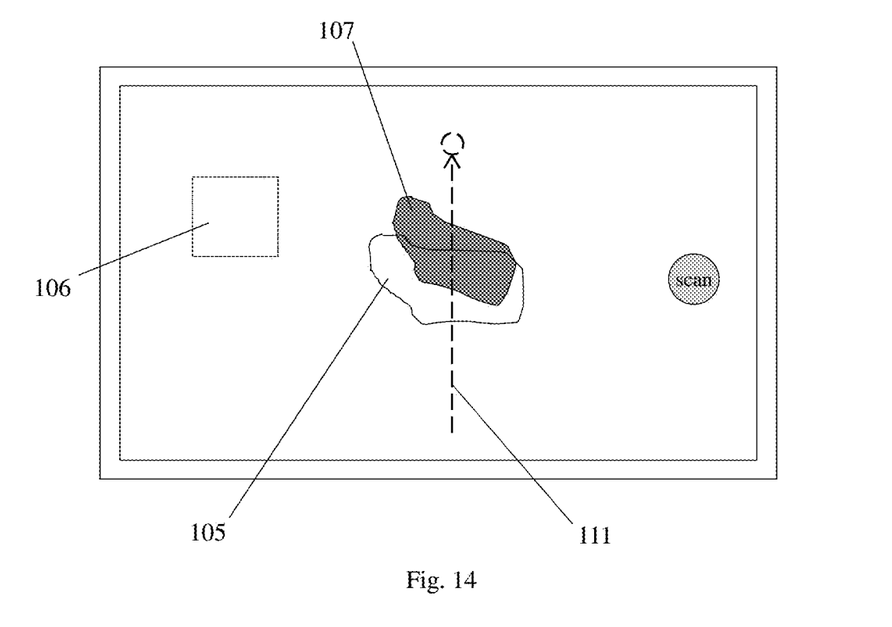

In addition (optional), in step S503, when displaying the 2D image on the viewfinder, the imaging device may display on the viewfinder an overlay of indications of the wound center and/or boundary and of the secondary reference regions that have been designated in the registration stage, using the retrieved data. FIG. 14 schematically illustrates an exemplary display in this step, showing an indication of previously captured wound boundary 105, an indication of the previously designated secondary reference region 106, an indication 111 of the head-toe direction relative to the previously captured wound boundary, and the image of the wound 107 currently being viewed on the viewfinder. The user can move or rotate the camera so that the viewing angle aligns with the head-toe direction indication 111, or until the current wound image 107 is aligned with the wound boundary indication 105. This helps to guide the user to capture the wound image in similar position and orientation as in the registered images.

Figure 15:
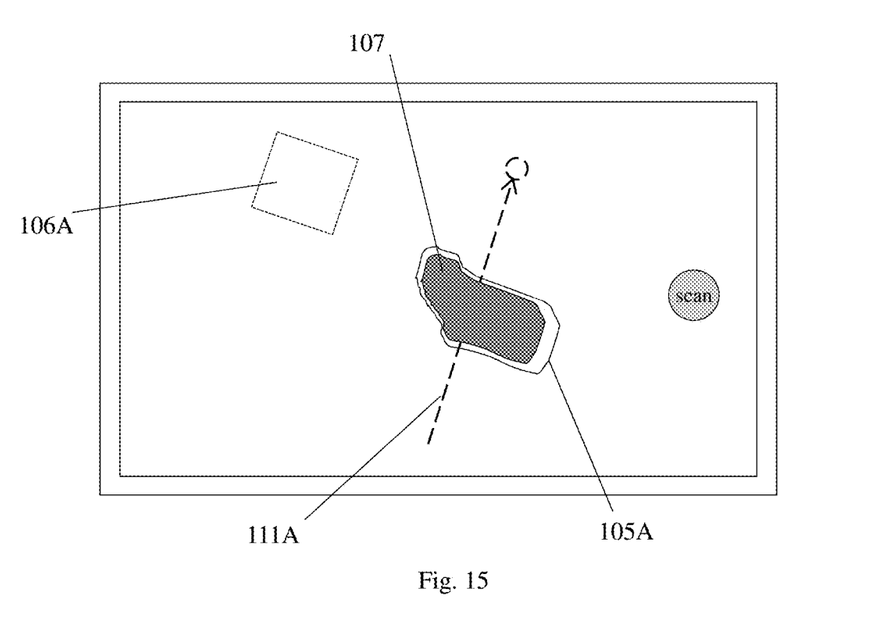

After capturing the image, the imaging device preliminarily detects the wound in the newly captured image, and rotates and shifts the wound boundary in the registered wound image so that it aligns with the wound in the newly captured image; based on this alignment, the regions in the newly captured wound image that correspond to the designated secondary reference regions of the registered wound image are identified as the secondary reference regions (step S507). In addition, as shown in the example of FIG. 15, the boundaries of the registered wound 105A and registered secondary reference region 106A (after rotation and shift) may be displayed as an overlay in the captured wound image, along with an indication 111A of the head-toe direction. In this example, the newly captured 107 is shown as being slightly smaller than the registered wound 105A as the wound may have changed.

The imaging device also performs color preliminary compensation for the wound image using the stored color balance, i.e. the color balance calculated based on the color checker in step S104 (step S508).

Referring back to FIG. 3, after capturing the image of the wound and its surrounding areas (including preliminary color compensation) and identifying the secondary reference regions, a color difference value between each secondary reference region in the newly captured (preliminarily color-compensated) wound image and the corresponding registered (preliminarily color-compensated) secondary reference region is calculated, and averaged to obtain an average color difference of the secondary reference regions (step S113). For example, equation (1) above may be used to calculate the color difference for each secondary reference region. Other color spaces may also be used to calculate color difference, such as XYZ. If the average color difference of the secondary reference regions is above a second predetermined threshold value (e.g., dE>3 when the RGB values are 0-255) ("yes" in step S113), the imaging device displays a warning message to guide the user to check imaging conditions e.g. ambient lighting, wound location, capture device settings, etc. (step S114) and the process goes back to step S112 to re-capture the wound image.

If the average color difference of the secondary reference regions is at or below the second predetermined threshold ("no" in step S113), the newly captured wound image is accepted, and the imaging device performs a second color compensation for the newly captured wound image using the color data of the newly captured and the registered baseline images (step S115). In this step, all images refer to the versions that have been preliminarily color-compensated in steps S104/S406/S508/S708.

Specifically, the imaging device estimates the RGB value of the current white balance Rw, Gw and Bw using the color values of the newly captured (step S108) and the registered baseline regions. For example, the following equations may be used, for each baseline region:

$$Rw=R0/R*255$$

$$Gw=G0/G*255$$

$$Bw=B0/B*255 \quad\quad (\text{Eq.2})$$

where R, G, B are the average color values of a newly captured baseline region and R0, G0, B0 are the average color values of the corresponding registered baseline region. The averages of the white balance values, Rwa, Gwa and Bwa, are calculated using the multiple baseline regions. Preferably, only the newly captured baseline regions that have color difference values below the first threshold (see step S109) are used here to calculate the average white balance.

Then, the average white balance values Rwa, Gwa and Bwa are used to compensate the color values of the wound image, by adjusting the color values of each image pixel using the average white balance values:

$$Rc(i)=R(i)*Rwa/255$$

$$Gc(i)=G(i)*Gwa/255$$

$$Bc(i)=B(i)*Bwa/255 \quad\quad (\text{Eq. 3})$$

where R(i), G(i) and B(i) are the color values of the i-th pixel of the newly captured wound image, and Rc(i), Gc(i) and Bc(i) are the compensated color values of the i-th pixel of the wound image. As a result, a color-compensated wound image is generated.

Wound assessment is then performed using the color-compensated wound image, and the results are stored on the server and/or the imaging device (step S116). Preferably, the same wound assessment procedure or algorithm (performed by the imaging device or the server) is used during the registration stage (step S106) and during each daily or routine procedures (step S116), so that the results can be compared to each other.

Noted that in the above-described method, all captured images, in both the registration stage and the wound assessment stage, are preliminarily color-compensated (see steps S104, S406, S508, and S708) using the same color balance, which is calculated using the color checker during the registration stage (step S104). This is based on the expectation that the same imaging device is used to capture all these images. During the wound assessment stage, the color comparison steps S109 (for baseline regions) and S113 (for secondary reference regions) are done using the preliminarily color-compensated images, and the second color compensation step S115 is done using the preliminarily color-compensated images.

Alternatively, in certain limited situations where the absolute color of the wound is not important, the preliminary color compensation steps S104, S406, S508, and S708, i.e. color compensation for all images based on the color checker, may be omitted; the color comparison steps S109 and S113 may be carried out based on un-compensated baseline and wound images. In such a case, the colors of all images would be affected by the white balance setting of the imaging device; but the color compensation step S115, which uses parts of the patient's body as baseline regions for color reference to perform color compensation, can still compensate for color variations among different wound images taken at different times, where the variations may be caused by, for example, lighting conditions, position of the body, etc.

It will be apparent to those skilled in the art that various modification and variations can be made in the wound image capture and self color compensation method and the image capture apparatus of the present invention without departing from the spirit or scope of the invention. Thus, it is intended that the present invention cover modifications and variations that come within the scope of the appended claims and their equivalents.

What is claimed is:

1. A method implemented in a system including an image capture device for using color images to assess a wound of a patient, comprising:
   during an initial registration stage:
   (a) displaying first messages which indicate parts of the patient's body as one or more baseline regions to be imaged, and capturing one or more first images containing the one or more baseline regions which are parts of the patient's body;
   (b) storing, in a database, the one or more first images and/or color data of the one or more first images;
   during a wound assessment stage subsequent to the initial registration stage:
   (c) retrieving, from the database, the one or more first images and/or color data of the one or more first images;
   (d) displaying second messages which indicate the same one or more baseline regions of the patient's body to be imaged, and capturing one or more second images containing the same one or more baseline regions of the same patient's body;
   (e) capturing a third image containing the wound and its surrounding area on the same patient's body;
   (f) calculate color compensation data by comparing color data of the second images and corresponding color data of the first images, and compensating color values of the third image based on the calculated color compensation data, the first, second and third images having been captured from the same patient's body; and
   (g) assessing the wound using the compensated third image containing the wound and its surrounding area.

2. The method of claim 1, wherein step (f) comprises:
   either calculating first average color values of the one or more baseline regions using the retrieved one or more first images, or retrieving first average color values of the one or more baseline regions from the database;
   calculating second average color values of the one or more baseline regions from the one or more second images;
   calculating average white balance values using the first average color values and the second average color values; and
   compensating color values of the third image using the average white balance values.

3. The method of claim 1,
   wherein in step (a), each of the captured one or more first images include a color checker imaged together with the baseline region, the color checker being a physical object having a plurality of color patches with known color values;
   the method further comprising:
   during the initial registration stage, after step (a):
   calculating a color balance which adjusts color values of the patches of the color checker in the one or more first images to the known color values of the corresponding patches of the color checker;
   compensating color values of the one or more first images using the calculated color balance; and
   storing the color balance in the database; and
   during the wound assessment stage, before step (f):
   retrieving the color balance from the database;
   compensating color values of the one or more second images using the retrieved color balance; and
   compensating color values of the third image using the retrieved color balance.

4. The method of claim 1,
   wherein step (a) includes, for each first image, designating a region of the first image as the baseline region, either by receiving a user input that designates the region, or by automatically selecting the region using a 3D image generated from the first image, the selected region being a flat region of the first image as determined using the 3D image;
   wherein step (b) includes storing, in the database, locations of the designated baseline regions of the first images; and
   wherein step (d) includes, for each second image, designating a region of the second image as the baseline region, either by receiving a user input that designates the region, or by automatically selecting the region using a 3D image generated from the second image, the selected region being a flat region of the second image as determined using the 3D image.

5. The method of claim 1, further comprising, during the wound assessment stage, after step (d) and before step (e):
   calculating a color difference value between each baseline region in the one or more first image and the corresponding baseline region in the one or more second images; and
   based on the calculated color difference values, determining whether to accept the one or more second images or to display an instruction to repeat step (d) to re-capture the one or more second images.

6. The method of claim 1, further comprising:
   during the initial registration stage:
   capturing a fourth image containing the wound and its surrounding area;
   designating one or more regions of the surrounding area of the fourth image as secondary reference regions; and
   storing, in the database, the fourth image and locations of the designated secondary reference regions of the fourth image.

7. The method of claim 6, further comprising:
during the wound assessment stage, before step (f):
retrieving, from the database, the fourth image and the locations of the designated secondary reference regions of the fourth image;
based on a comparison of the third image and the fourth image and based on the locations of the designated secondary reference regions of the fourth image, determining one or more regions of the surrounding area of the third image as secondary reference regions corresponding to the secondary reference regions of the fourth image;
calculating a color difference value between each secondary reference region of the third image and the corresponding secondary reference region of the fourth image; and
based on the calculated color difference values, determining whether to accept the third image or to display an instruction to repeat step (e) to re-capture the third image.

8. The method of claim 6,
wherein the step of capturing a fourth image includes generating a 3D image containing the wound and its surrounding areas, and
wherein the designating step includes: based on the 3D image, automatically selecting one or more regions in the fourth image as the secondary reference regions, the selected regions being on a same plane as the wound as determined using the 3D image.

9. The method of claim 6, wherein step (e) includes: overlaying on a viewfinder of the image capture device an indication of a boundary of the wound in the fourth image and an indication of the locations of the secondary reference regions of the fourth image.

10. A computer program product comprising a computer usable non-transitory medium having a computer readable program code embedded therein for controlling an image capture device, the computer readable program code configured to cause the image capture device to execute a process for using color images to assess a wound of a patient, the process comprising:
during an initial registration stage:
(a) displaying first messages which indicate parts of the patient's body as one or more baseline regions to be imaged, and capturing one or more first images containing the one or more baseline regions which are parts of the patient's body;
(b) storing, in a database, the one or more first images and/or color data of the one or more first images;
during a wound assessment stage subsequent to the initial registration stage:
(c) retrieving, from the database, the one or more first images and/or color data of the one or more first images;
(d) displaying second messages which indicate the same one or more baseline regions of the patient's body to be imaged, and capturing one or more second images containing the same one or more baseline regions of the same patient's body;
(e) capturing a third image containing the wound and its surrounding area on the same patient's body;
(f) calculate color compensation data by comparing color data of the second images and corresponding color data of the first images, and compensating color values of the third image based on the calculated color compensation data, the first, second and third images having been captured from the same patient's body; and
(g) assessing the wound using the compensated third image containing the wound and its surrounding area.

11. The computer program product of claim 10, wherein step (f) comprises:
either calculating first average color values of the one or more baseline regions using the retrieved one or more first images, or retrieving first average color values of the one or more baseline regions from the database;
calculating second average color values of the one or more baseline regions from the one or more second images;
calculating average white balance values using the first average color values and the second average color values; and
compensating color values of the third image using the average white balance values.

12. The computer program product of claim 10,
wherein in step (a), each of the captured one or more first images include a color checker imaged together with the baseline region, the color checker being a physical object having a plurality of color patches with known color values;
the process further comprising:
during the initial registration stage, after step (a):
calculating a color balance which adjusts color values of the patches of the color checker in the one or more first images to the known color values of the corresponding patches of the color checker;
compensating color values of the one or more first images using the calculated color balance; and
storing the color balance in the database; and
during the wound assessment stage, before step (f):
retrieving the color balance from the database;
compensating color values of the one or more second images using the retrieved color balance; and
compensating color values of the third image using the retrieved color balance.

13. The computer program product of claim 10,
wherein step (a) includes, for each first image, designating a region of the first image as the baseline region, either by receiving a user input that designates the region, or by automatically selecting the region using a 3D image generated from the first image, the selected region being a flat region of the first image as determined using the 3D image;
wherein step (b) includes storing, in the database, locations of the designated baseline regions of the first images; and
wherein step (d) includes, for each second image, designating a region of the second image as the baseline region, either by receiving a user input that designates the region, or by automatically selecting the region using a 3D image generated from the second image, the selected region being a flat region of the second image as determined using the 3D image.

14. The computer program product of claim 10, wherein the process further comprises, during the wound assessment stage, after step (d) and before step (e):
calculating a color difference value between each baseline region in the one or more first image and the corresponding baseline region in the one or more second images; and
based on the calculated color difference values, determining whether to accept the one or more second images or to display an instruction to repeat step (d) to re-capture the one or more second images.

15. The computer program product of claim 10, wherein the process further comprises:
during the initial registration stage:
capturing a fourth image containing the wound and its surrounding area;
designating one or more regions of the surrounding area of the fourth image as secondary reference regions; and
storing, in the database, the fourth image and locations of the designated secondary reference regions of the fourth image.

16. The computer program product of claim 15, wherein the process further comprised:
during the wound assessment stage, before step (f):
retrieving, from the database, the fourth image and the locations of the designated secondary reference regions of the fourth image;
based on a comparison of the third image and the fourth image and based on the locations of the designated secondary reference regions of the fourth image, determining one or more regions of the surrounding area of the third image as secondary reference regions corresponding to the secondary reference regions of the fourth image;
calculating a color difference value between each secondary reference region of the third image and the corresponding secondary reference region of the fourth image; and
based on the calculated color difference values, determining whether to accept the third image or to display an instruction to repeat step (e) to re-capture the third image.

17. The computer program product of claim 15,
wherein the step of capturing a fourth image includes generating a 3D image containing the wound and its surrounding areas, and
wherein the designating step includes: based on the 3D image, automatically selecting one or more regions in the fourth image as the secondary reference regions, the selected regions being on a same plane as the wound as determined using the 3D image.

18. The computer program product of claim 15, wherein step (e) includes: overlaying on a viewfinder of the image capture device an indication of a boundary of the wound in the fourth image and an indication of the locations of the secondary reference regions of the fourth image.

* * * * *